United States Patent [19]

Glover

[11] Patent Number: 5,013,740
[45] Date of Patent: May 7, 1991

[54] METHOD FOR TREATING EMOTIONAL NUMBNESS AND COMA

[76] Inventor: Hillel Glover, 500 E. 77th St., #439, New York, N.Y. 10021

[21] Appl. No.: 519,112

[22] Filed: May 4, 1990

Related U.S. Application Data

[63] Continuation-in-part of Ser. No. 497,544, Mar. 22, 1990.

[51] Int. Cl.⁵ ............................................. A01H 43/42
[52] U.S. Cl. ..................................... 514/282; 514/921
[58] Field of Search ................................ 514/282, 921

[56] References Cited

U.S. PATENT DOCUMENTS

| | | | |
|---|---|---|---|
| 4,267,182 | 5/1981 | Holaday et al. | 514/282 |
| 4,882,335 | 11/1989 | Sinclair | 514/282 |
| 4,906,637 | 3/1990 | Fader | 514/282 |

*Primary Examiner*—Stanley J. Friedman
*Assistant Examiner*—Theodore J. Criares
*Attorney, Agent, or Firm*—Ostrolenk, Faber, Gerb & Soffen

[57] ABSTRACT

An opiate antagonist or a pharmaceutically acceptable salt thereof is used to treat emotional numbness associated with Post Traumatic Stress Disorder and other psychopathologic conditions. Opiate antagonist or a pharmaceutically acceptable salt thereof is also used to treat coma.

11 Claims, No Drawings

METHOD FOR TREATING EMOTIONAL NUMBNESS AND COMA

This application is a continuation-in-part of U.S. patent application Ser. No. 07/497,544 filed Mar. 22, 1990.

BACKGROUND OF THE INVENTION

1. Field of the Invention

The present invention relates to the use of opiate antagonists to treat psychopathologic conditions, more particularly, the use of opiate antagonists to treat emotional numbness associated with Post Traumatic Stress Disorder (PTSD) and other psychopathologic conditions. Emotional numbness is conceptualized as a biopsychological response to extreme emotional or physical trauma.

The present invention also relates to the use of opiate antagonists to treat coma.

2. Description of the Related Prior Art

At this time, there is no pharmacological treatment available for the psychiatric condition of emotional numbing.

The principal feature of emotional numbness is a person's subjective experience of the inability to feel emotions, and is accompanied by a lack of care and concern for self and others. When numbness is profound no feeling can be experienced and the person takes on a "wooden" expressionless and lifeless appearance. Numb individuals are generally unresponsive to the environment and they are socially withdrawn. Unresponsiveness to the environment is a composite disturbance representing a diminished level of mental alertness and awareness and a loss of interest in the outside world. Numb individuals do not experience an empathic bond or a sense of relatedness to others. In social situations they tend to feel alienated and apart. Emotional numbness is frequently associated with numbness and/or paresthesias of the body and feelings of heaviness or paralysis. Severe numbness is accompanied by a profound impairment of concentration and memory with an amnesia for events occurring during the numb state. Information processing of any kind may be severely impaired. When emotional numbness is severe and prolonged, it is usually accompanied by a lack of motivation, interest or pleasure in life's activities. Numb individuals are thus emotionally, mentally, psychologically and socially impaired. They are less able to deal with stresses of any kind — especially reminders of their past traumatic experiences. They tend, therefore, to avoid thoughts or feelings and activities or situations which might activate recollections of the original traumatic event(s). The one exception to this last statement is the tendency for some numbed individuals to at times actively seek out exciting or (very) dangerous activities in order to overcome their numbness and to experience feeling alive (see below).

The presence of numbing is evaluated clinically as part of the psychiatric diagnosis of PTSD. No independent laboratory tests currently exist to identify the presence or absence of numbing. Numbing (and avoidance) is one of four categories of psychiatric disturbance that must be fulfilled for an individual to receive the diagnosis of PTSD. The American Psychiatric Association's Diagnostic Statistical Manual's (DSMR III-R) definition of numbing (and avoidance) includes seven items, any three of which have to be present for that category (numbing and avoidance) to be fulfilled. Emotional numbness is specifically represented by two of seven items. One item describes the presence of a restricted range of affect, e.g., the inability to have loving feelings. A second item describes a markedly diminished interest in significant activities. Numbing is defined by this Manual as "persistent avoidance of stimuli associated with the trauma or numbing of general responsiveness (not present before the trauma), as indicated by at least three of the following:

(1) efforts to avoid thoughts or feeling associated with the trauma (2) efforts to avoid activities or situations that arouse recollections of the trauma (3) inability to recall an important aspect of the trauma (psychogenic amnesia)

(4) markedly diminished interest in significant activities (in young children, loss of recently acquired developmental skills such as toilet training or language skills)

(5) feeling of detachment or estrangement from others (6) restricted range of affect, e.g., unable to have loving feelings (7) sense of foreshortened future, e.g., does not expect to have a career, marriage, or children or a long life."

The above conditions are clinical conditions exhibited by an individual which are criteria a health care provider would look to during the psychiatric diagnosis.

Emotional numbing is primarily a subjective complaint. Emotional numbness can vary along three parameters: duration, severity, and social context. Numbness can be experienced for minutes, hours, days, months or years on a continuous or intermittent basis. A person who has severe or profound emotional numbing does not have any feelings at all. In a less severe case, emotions associated with high levels of physiological arousal may be experienced: e.g., rage, fear, and vulnerability. However, tender affectionate feelings are not felt. For periods of time, some less severely numbed individuals may be able to experience love and concern towards a specific individual(s). This may be a child, trusted spouse or fellow survivor of a traumatic episode.

Emotional numbing may be accompanied by a physical experience of heaviness or paralysis of the body, pins and needles, tingling or numbness of parts of the body, feelings of unreality, alienation, and detachment from others. Cognitive disturbances can include mental confusion, amnesia, impaired concentration, indecisiveness, inability to plan future actions, and a paralysis of will. These cognitive disturbances may occur independent of the level of physiological arousal or distress; forgetfulness, disorientation, or confusion can occur without any apparent preceding increase in stress or anxiety.

Some patients are not able to make the distinction between the mental states of numbness and depression. Impaired cognitions, including an absence of self awareness, may interfere with an individual's ability to distinguish between numbness and depression. Other individuals may frequently shift between states of depression and numbness which makes it difficult for them to distinguish their subjective experiences. Numbness and depression also share certain symptoms including impaired concentration and memory and lack of interest and pleasure in life's activities. Emotional numbness should be distinguished from depression. Emotional numbness denotes an absence of feelings (including those of depression and sadness). In contrast to a depressed person, a numbed individual lacks feelings of regard, concern, caring or empathy for himself/herself and others. Common terms which traumatized persons use to describe this numb state of mind include: shutdown, numb, ice cold, hollow, dead, empty and no feelings, care or concern for anyone or anything. Family members commonly regard relations who are numb as being cold, heartless, and emotionally unresponsive. A profoundly numb individual has a wooden facial expression rather than one that is depressed. Very occasionally the emotionally numbed individual may appear to be angry or sad to others, yet respond with bewilderment or denial when questioned about his/her look of anger or sadness.

Numbed persons may learn to role play appropriate behavioral responses in family and social settings even though they continue to have no feelings. When questioned, these individuals may relate what they thought they should have felt based on their inferences and judgments about the situation rather than what they actually experienced.

The mental state of emotional numbness is a disabling condition for the traumatized victim and his or her family members. Numbness interferes with a person's ability to enjoy and participate in life's activities (work, intimacy, sex, etc.) and with the individual's ability to respond with genuine affection, interest or concern about anybody or anything, which can oftentimes lead to marital and family discord. Although a numbed individual may be less likely to respond emotionally to most situations, the same individual may be more likely to lash out than to exercise restraint once enraged because of his/her indifference to the consequences of his/her actions. In addition, rage can also precipitate or intensify the numb response.

When numbed individuals do experience negative emotions such as rage, bitterness, hostility or betrayal, these mood states continue for extended periods of time. However, emotions that are positively felt decay rapidly and evaporate.

Some individuals with emotional numbing may seek out sensation and risk-taking activities such as skydiving, racing cars, gambling, drug abuse, self-inflicted pain, etc. in an effort to escape the deadening effect of numbness. These activities can assume a compelling addictive drive accompanied by intense feelings of craving.

Endogeneous opiates (endorphins) are actively produced in the central nervous system (CNS) in response to stress. Endorphins represent one of the primarily major inhibitory neurotransmitter systems, inhibiting the release of other neurotransmitters, both in the CNS and in the peripheral organs. Endorphins can inhibit the neural transmission of sensory information in the spinal cord. Endorphins have been strongly implicated in the experimental paradigm of stress induced analgesia. Conditioned stress induced analgesia is believed to be specifically endorphin dependent.

Exogenous opiates demonstrate a variety of effects on the mood and behavior of animals and man depending on dose, chronicity, method, site and timing of administration (in relation to exposure to stress). Responses may vary from calm sedation and euphoria to dysphoria and agitation. Opiates are well known for their ability to cause mental confusion, apathy and reduction of anxiety associated with pain.

The limbic system of the CNS is where emotions, motivations and interests are processed and modulated. It is a region densely populated with opiate receptors. In PTSD endorphins are postulated to shut down the processing of emotional experiences and motivational systems which leads to numbness and loss of interest.

The hippocampus is a structure within the limbic system which is considered important for memory processing, including the consolidation and establishment of long term memory. Amnesia is classically associated with damage to the medial temporal brain region, especially the hippocamus formation. This region, in turn, has extensive projections to specific sensory modality pathways and polymodal areas in the neocortex where long term memory storage probably occurs. These areas are also densely occupied by opiate receptors. Opiates have also been found to be capable of inducing amnesia in experimental animals. Excessive secretion of endorphins in these regions are hypothesized to lead to symptoms of mental confusion, disorientation and amnesia.

States of numbness are similarly postulated to occur in other psychopathological conditions. These include affective disorders such as "masked" depression and severe or psychotic depression. The latter condition is generally unresponsive to antidepressants but is responsive to electric shock therapy. Opiate antagonist medication provides an alternative to that form of intervention for many of these individuals. A number of psychological and clinical states may produce apathy which, by definition, includes the absence of emotions. When apathy is not the result of organic degeneration of the central nervous system it should similarly be considered for opiate antagonist treatment. Severely anxious individuals and those with hypochondriacal and psychosomatic conditions may experience numbness. Alexithymia, a condition in which individuals are unable to describe their feelings verbally, is observed in persons with the diagnosis of PTSD and in persons with psychosomatic disorders. It is postulated that a percentage of individuals with alexithymia manifest this difficulty as a result of emotional numbness. Furthermore, schizophrenic conditions in which negative symptoms including apathy predominate also experience emotional numbness. In all these conditions, numbness represents an extreme biopsychological response to the stress of emotional overload so that the emotional experience is profoundly dampened down or turned off and the expenditure of metabolic energy is reduced. The numb state, however, creates additional problems of its own (as described above). Numbness can become the principal response to any nonspecific situation in which an individual feels vulnerable and/or unable to cope. This is especially true of the PTSD population, where the numb response is likely to become a chronic and persistent problem.

Nalmefene is a known narcotic antagonist.

U.S. Pat. Nos. 3,814,768 and 3,896,226 both to Fishman disclose nalmefene and its pharmaceutically acceptable salts per se and as a component in narcotic antagonist compositions, respectively.

Compounds related to nalmefene, i.e., having the same pentacyclic nucleus, including naloxone, naltrexone, nalbuphine, thebaine, etc., are also known and are used to treat mental illness.

U.S. Pat. No. 4,388,324 to Horrobin discloses the use of certain opiate antagonists, e.g., naloxone to enhance the prostaglandin (seris 1) levels which are suggested to thereby indirectly influence schizophrenia and depression.

U.S. Pat. No. 3,717,643 to Archer discloses the use of certain morphine derivatives as central nervous system stimulants. U.S. Pat. No. 3,299,072 to Bartels-Keith discloses the use of certain thebaine derivatives for the same purpose.

U.S. Pat. No. 3,282,050 to Buckett et al. discloses the use of certain morphine derivatives as tranquilizers or psychosedatives.

U.S. Pat. Nos. 4,154,142 and 4,511,570 disclose the use of a particular normorphone derivative to treat hyperkinetic children and senile adults, respectively.

SUMMARY OF THE INVENTION

It is an object of the present invention to provide a novel method for treating emotional numbness associated with PTSD and other psychopathologic conditions.

This objective and other objectives are achieved by providing a method comprising administering to a patient in need thereof an effective amount of an opiate antagonist or a pharmaceutically acceptable salt thereof, preferably in combination with a pharmaceutically acceptable carrier. Preferably, the opiate antagonist is an opiate antagonist having a pentacyclic nucleus, most preferably, nalmefene, naloxone, naltrexone, nalbuphine, or thebaine. Preferably, nalmefene is administered orally in an initial dosage of about 0.5 to 1.0 mgms. b.i.d. for about one week, followed by a dosage of about 1.0 to 5.0 mgms. b.i.d. for about one week, followed by a dosage of about 5.0 to 10.0 mgms. b.i.d. for about one week, followed by a dosage of about 10.0 to 20.0 mgms. b.i.d. for about one week. The dosage is increased by about 10.0 to 20.0 mgms. every week thereafter until the patient has achieved a numb-free state.

Symptoms related to the emotional numbness, i.e., conditions exhibited by an individual which are a byproduct of the emotional numbness, such as somatic numbing, pins and needles, lack of empathy, avoidance, mental confusion, amnesia, loss of interest and compulsive sensation seeking behavior are reduced by the method of the invention. The emotional numbness itself may be associated with one or more psychopathologic conditions, such as PTSD, depression, hypochondria, anxiety, a psychosomatic disorder, depersonalization disorder or negative symptoms of schizophrenia, or the emotional numbness may be associated with one or more physical insults to the central nervous system such as a closed head injury or a cerebral vascular accident.

It is another object of the invention to provide a novel method for treating coma.

This objective and other objectives are achieved by providing a method comprising administering to a patient in need thereof an effective amount of an opiate antagonist or a pharmaceutically acceptable salt thereof, preferably in combination with a pharmaceutically acceptable carrier. Preferably the opiate antagonist is an opiate antagonist having a pentacyclic nucleus, most preferably, nalmefene, naloxone, naltrexone, nalbuphine, or thebaine. The opiate antagonist is preferably administered intravenously, intramuscularly or subcutaneously in an initial dosage of about 2 mgs. with about a doubling of the dose about every 2 hours until the patient is alert and responsive to questions.

DETAILED DESCRIPTION OF THE PREFERRED EMBODIMENT

In general, the present invention relates to the use of opiate antagonists for the treatment of emotional numbness associated with PTSD and other psychopathologic conditions, and the use of opiate antagonists for the treatment of coma.

It has been discovered that when emotional numbness is overcome in accordance with the method of the invention, certain secondary characteristics or symptoms related to or derived from the emotional numbness begin to disappear or at least begin to lessen significantly. In other words, when emotional numbness is successfully treated, then other conditions or symptoms associated with it are also treated. Some of these by-product conditions or symptoms of emotional numbness include, but are not limited to, somatic numbing, pins and needles, lack of empathy, mental confusion, amnesia, loss of interest, and compulsive sensation seeking behavior. The emotional numbing itself may be associated with PTSD or any other psychopathologic condition including, but not limited to, depression, hypochondria, anxiety, a psychosomatic disorder and negative symptoms of schizophrenia. Moreover, the emotional numbness may be associated with any of various physical insults to the central nervous system, such as, but not limited to, closed head injuries and cerebral vascular accidents.

Although any suitable opiate antagonist may be employed, an opiate antagonist having a pentacyclic nucleus, such as nalmefine, naloxone, naltrexone, nalbuphine or thebaine, is preferred. Of these opiate antagonists, nalmefene is most preferred.

Nalmefene (6-methylene-6-desoxy-N-cyclopropylmethyl-14-hydronormorphine) is derived by the Wittig reaction from naltrexone. See Hahn et al., J. Med. Chem. 18, 259 (1975). See also U.S. Pat. Nos. 3,814,768 and 3,896,226, both disclosures of which are hereby incorporated by reference. Suitable nalmefene for use in the method of the invention is commercially available in its hydrochloride salt form from Ivax, 8800 Northwest 36th Street, Miami, Fla, 33178. Nalmefene has the following formula:

While not wishing to be bound by theory, it is believed that the exocyclic methylene group at position 6 of the molecule enhances oral bioavailability and potency of the drug by blocking one of its sites of metabolism.

This compound is particularly effective by the oral route and is also effective when administered parenterally, although any suitable route may be employed. The compound is preferably combined (mixed) with a pharmaceutically acceptable inert carrier for easy ingestion, and because nalmefene has a high potency in small dosages. Suitable inert carriers include, but are not limited to, water, milk optionally with sugar and/or starch, natural and synthetic fruit juices, such as orange juice, grapefruit juice, grape juice, pineapple juice, lemon juice and prune juice, and sweetened beverages such, for instance, as flavored water with or without carbonation. If the compound is to be administered orally, one of the above carriers is desirable. If the compound is to be administered parenterally, distilled water is a desirable carrier. The compound also may be administered rectally by incorporation in a standard suppository. Other routes of administration and suitable pharmaceutically acceptable carriers therefor will be apparent to one skilled in the art.

The method of the invention is recommended for any individual who has PTSD and/or other psychopathologic conditions noted above, in whom numbness is persistent and interferes with that person's ability to enjoy life's activities and to relate to significant others. Administration of an opiate antagonist in accordance with the invention is preferably instituted at the lowest possible oral dose to be followed by weekly incremental doses until numbing is reversed. Benzodiazepines, clonidine and other medications used in the treatment of opiate withdrawal symptoms will generally be needed to control any resulting distresses (e.g., increased symptoms of anxiety, palpitations, insomnia, abdominal pain, and diarrhea) until adequate opiate blockade is achieved. Specific dosages are a function of the intensity and persistence of numbing, the degree of continuing external stressors and the intensity of associated levels of physiological arousal. The final dose to reverse the effect of numbing will be significantly higher than the dose used to precipitate withdrawal reactions in a narcotic addict. Opiate blockade in the PTSD individual preferably is maintained at a high dose level because endorphins are constantly being manufactured within the brain as part of a conditioned neurochemical response. Maintenance dosage is preferably continued for at least one year before a trial of gradual reduction is attempted. During that period, the individual should have shown an ability to consistently relate to significant others and to experience feelings rather than numbness.

Dosage changes may be instituted relatively quickly as long as the patient is followed carefully on a weekly basis and is informed in advance of temporary increases of emotional and physical symptoms Patients who are administered clonidine should be provided with the means to take their blood pressure on a regular basis.

Preferably, in the method of the invention, the patient is started on nalmefene at about 0.5 to 1.0 mgm. b.i.d., raised to 1.0 to 5.0 mgms. b.i.d. the following week, then to 5.0 to 10.0 mgms. b.i.d. the third week, and to 10.0 to 20.0 mgms. b.i.d. the fourth week, with 10.0 to 20.0 mgm. increases per week thereafter. Most preferably, an opiate antagonist is started at about 0.5 mgm. b.i.d., raised to about 1 mgm. b.i.d. the following week, then to 5 mgms. b.i.d. the third week and to about 10 mgms. b.i.d. the fourth week, with about 20 mgm. increases per week thereafter.

Patients should keep daily logs of their numb state, the presence or absence of nightmares, flashbacks, intrusive thoughts, startle responses, and their respective intensities. Weekly records should be kept of the patient's level of anxiety and mood states. Patients with significantly higher baseline levels of anxiety and who have to be maintained on mild tranquilizers will require more careful supervision, larger doses of a tranquilizer and higher doses of opiate antagonist before their numbness is reversed. Some individuals may require doses of opiate antagonist that would be greater than 100 mgms. b.i.d. It should be emphasized that in the process of increasing the dose of opiate antagonist, any symptom associated with PTSD may worsen before it improves. As the dose of the drug is increased, patients will commonly experience increased feelings of emotional vulnerability. Some symptoms in some individuals may persist for a longer period of time before they reverse. This drug may make some individuals temporarily more numb, especially when administered to persons who are anxious. It will be understood by those skilled in this field that the dosage may be varied to accommodate individual needs, reactions or circumstances. Also, clinically obese individuals should not be administered the drug because they experience intensely adverse reactions of rage and/or anxiety at very low doses. In general, a significantly large dose increase is required to go from a good to a 100% no-numbness response.

The use of an opiate antagonist to treat coma in accordance with the invention will now be described.

Some forms of coma are postulated to be induced and/or maintained by the hypersecretion of endorphins. As previously described in the text, the profound numb state is associated with a general reduction in the level of a traumatized person's alertness and awareness to the environment. Thus, numbness represents some degree of impairment in an individual's level of consciousness. It should be restated that endorphins are secreted when an individual is exposed to a variety of emotional and physical stressors. Coma can be readily induced with an overdose of exogenously administered opiates. Similarly, the opiate induced comatose state can be readily reversed with the administration of an opiate antagonist. Hibernation in animals is a physiological state which bears striking similarities to coma, and it too can be readily reversed with an opiate antagonist. Head trauma may also cause a loss of consciousness with possible numbness upon awakening from coma.

A number of comatose individuals remain in their vegetative states even after the original insults to their brains and their immediate sequalae have been resolved. This is most apparent, for example, in certain vascular lesions and cases of closed head injuries in which there is no significant irreversible damage to essential brain structures (i.e., brain stem) and brain edema is no longer present. Persons in a comatose state have spontaneously awakened months and even years later. There is no known intervention to bring these individuals out of coma. Opiate antagonists are therefore recommended in accordance with the invention for persons in a comatose state in which no obvious explanation for the persistence of the coma can be established.

Administration of an opiate antagonist should initially be done either intravenously, intramuscularly or subcutaneously in combination with any suitable pharmaceutically acceptable carrier. Naloxone 2 mgms. per dose can be used with a doubling or a significant increase of the dose repeated every 2 hours until the person is alert and responsive to questions. At that time, the person can be switched to a comparable dose of nalmefene which is taken orally in combination with any suitable pharmaceutically acceptable carrier. Dosages can be lowered gradually as the patient's condition remains stable over a protracted period of time. It will be understood that different individuals in a vegetative state may require very different doses of opiate antagonist to effect a change in their comatose states. They may also require different maintenance dosages and regimens of oral opiate antagonist. It will be understood by those skilled in this field that the dosage may be varied to accommodate individual needs, reactions or circumstances. Before administering opiate antagonists every medical and/or surgical cause for the persistent vegetative state should be evaluated and treated.

The invention will be more fully understood by reference to the following examples. Examples 1 and 2 are directed to treating emotional numbness. Example 3 is directed to treating coma.

EXAMPLE 1

John Doe is a 44-year old married Vietnam combat veteran who served as a medic during the war. He was exposed to several life-threatening experiences in addition to his emergency medical treatment responsibilities. Mr. Doe has been emotionally numb since his discharge from service in Vietnam. He began to experience nightmares and flashbacks after a visit to the Washington Vietnam Memorial War in 1984. Subsequent to that date, Mr. Doe was diagnosed to have PTSD as a result of his exposure to trauma in the Vietnam War.

John Doe evidenced persistent numbing on a daily basis prior to starting on nalmefene 1 mgm. b.i.d. Baseline subjective level of tension was rated to be moderate. Mr. Doe was not on any tranquilizer. The dosage of nalmefene was increased 2 mgms./day, twice a week. The patient complained of episodic symptoms of anxiety, restlessness, irritability, abdominal pain and insomnia until the dosage was increased to 28 mgms. b.i.d. Symptoms either worsened or improved with dosage increases. Emotional numbness showed considerable variation from day to day with a gradual increase in the number of numb-free days. Mr. Doe was able to maintain a relatively symptom (anxiety) free state with occasional limited periods of numbness for one month on a dose of 28 mgms. b.i.d. Anxiety symptoms up to that dose had been controlled with a mild tranquilizer and clonidine 0.1 mgm. as needed. The patient became severely numb again when he was told that his wife would require major surgery. Nalmefene was increased once again to 2 mgms./day on twice a week basis. Surgery was successful but the patient continued to experience considerable numbness with feelings of vulnerability and diminished sex drive. Mr. Doe's condition began to improve at the dose of 41 mgms. b.i.d. At that time, he was informed that his mother had a recurrence of cancer. Numbness once again significantly worsened with the appearance of panic attacks, restlessness, social withdrawal, insomnia, and impaired concentration and memory. His condition stabilized once again at a dose of 47 mgms. b.i.d. with only occasional restless sleep and intermittent anxiety. It should be noted that this patient's nightmares and flashbacks essentially disappeared once he was started on nalmefene at the beginning of the protocol. These symptoms briefly returned when his condition deteriorated during his wife's convalescence from surgery. The dosage was increased 4 mgms./day — from 47 mgms. b.i.d. to 55 mgms. b.i.d., and then increased by 10 mgms./day from 55 mgms. to 60 mgms. b.i.d. An additional major stressor experience required raising the dose to 80 mgms. bid. This patient has maintained a numb-free state with no anxiety symptoms or complaints of sluggishness at this dosage.

EXAMPLE 2

Jane Smith is a 38-year old woman married to a disabled Vietnam combat veteran who has the diagnosis of PTSD. Mrs. Smith's mother and younger brother are both psychotic. They live on the second floor of the two-family house in which the Smith couple reside. Jane Smith has always been regarded as the most resilient and responsible member of the family. She, in turn, has always considered it to be her obligation to look after the needs of the other family members. Mrs. Smith was in marital counseling with her husband when she began complaining of increasing emotional numbness and an inability to care for others. Mrs. Smith was administered Trexan (naltrexone hydrochloride), 25 mgms. per day for one week after baseline liver enzymes were found to be normal. She then reported feeling more alert, but experienced intermittent symptoms of light-headedness and interrupted sleep. Trexan was increased to 50 mgms. per day during the second week. She then reported feeling more energetic, had mild anxiety, diminished sluggishness and increased access to her emotions, especially feelings of anger and resentment towards family members for their persistent demands. Mrs. Smith's dosage was increased on the third week, for the last increase to 75 mgms. per day. She reported feeling calmer, more confident, and no longer numb. Sleep was restful and no longer interrupted. It was decided to maintain her on that dose for 3-6 months in order to enable Mrs. Smith to deal more confidently with her family members. During that period of time, Mrs. Smith became depressed. She was then begun on a tricyclic anti-depressant. Mrs. Smith showed a very positive response to the tricyclic anti-depressant, which would not have helped her during the numb state.

EXAMPLE 3

John Johnson is a 33-year old single male who became comatose as the result of a head trauma he received in a motor vehicle accident. Until one month after the accident he remained in a vegetative state with no sign of eye opening or motor response to pain. There was no evidence of brain edema or fever, and laboratory results ruled out any metabolic dysfunction. CT scans revealed no evidence of hemorrhage edema, infarction or herniation. The patient's fluid intake and output was closely monitored. The patient was administered 2 mg. naloxone intravenously. The dosage was doubled every two hours until the patient was alert, responsive to questions and able to sit up by himself. This occurred at a dose of 32 mgms. Mr. Johnson was then switched to an approximately equivalent dose of nalmefene, 250 mgms. every 12 hours. He was maintained on this dose for six months with no side effects other than occasional mild symptoms of light-headedness. The dose of nalmefene was reduced 10 mgm/dose per month until it was discontinued, in view of no evidence of any deterioration in the level of alertness and attention or impairment of his higher cortical functions.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for treating vegetative state due to closed head injury or cerebral vascular accident, comprising administering to a patient in need thereof an effective vegetative state reversing amount of an opiate antagonist or a pharmaceutically acceptable salt thereof.

2. The method of claim 1, wherein the opiate antagonist is an opiate antagonist having a pentacyclic nucleus.

3. The method of claim 2, wherein the opiate antagonist is selected from the group consisting of nalmefene, naloxone, naltrexone, nalbuphine and thebaine.

4. The method of claim 3, wherein the opiate antagonist is nalmefene.

5. The method of claim 3, wherein the opiate antagonist is naloxone.

6. The method of claim 3, wherein the opiate antagonist is naltrexone.

7. The method of claim 3, wherein the opiate antagonist is nalbuphine.

8. The method of claim 3, wherein the opiate antagonist is thebaine.

9. The method of clam 1, wherein the administration is intravenously, intramuscularly or subcutaneously.

10. The method of claim 1, wherein the effective vegetative state reversing amount comprises an initial dosage of about 2 mgms. followed by a doubling of the dose about every 2 hours until the patient is alert and responsive to questions.

11. The method of claim 1, wherein the opiate antagonist or pharmaceutically acceptable salt thereof is administered in combination with a pharmaceutically acceptable carrier.

* * * * *